United States Patent
Ochiai et al.

(10) Patent No.: US 9,192,404 B2
(45) Date of Patent: Nov. 24, 2015

(54) DEVICE AND METHODS FOR USE DURING ARTHROSCOPIC SURGERY

(75) Inventors: Derek H. Ochiai, Great Falls, VA (US); Paul Alexander Torrie, Marblehead, MA (US)

(73) Assignee: Smith & Nephew, Inc., Memphis, TN (US)

(*) Notice: Subject to any disclaimer, the term of this patent is extended or adjusted under 35 U.S.C. 154(b) by 0 days.

(21) Appl. No.: 13/246,799

(22) Filed: Sep. 27, 2011

(65) Prior Publication Data

US 2012/0157999 A1      Jun. 21, 2012

Related U.S. Application Data

(60) Provisional application No. 61/386,718, filed on Sep. 27, 2010.

(51) Int. Cl.
| A61B 17/3211 | (2006.01) |
| A61B 17/32 | (2006.01) |
| A61B 17/22 | (2006.01) |

(52) U.S. Cl.
CPC ..... *A61B 17/320016* (2013.01); *A61B 17/3211* (2013.01); *A61B 2017/22038* (2013.01); *A61B 2017/22039* (2013.01); *A61B 2017/320052* (2013.01)

(58) Field of Classification Search
CPC .......... A61B 17/32; A61B 17/320016; A61B 17/3209; A61B 17/32093; A61B 17/3211; A61B 17/3213; A61B 17/8897; A61B 2017/320024; A61B 2017/320056; A61B 2017/32113; A61B 2017/32116; A61B 2017/00469; A61B 5/6581
USPC .......... 606/79, 83, 84, 86 R, 89, 90, 170, 181
See application file for complete search history.

(56) References Cited

U.S. PATENT DOCUMENTS

| 4,580,563 | A | 4/1986 | Gross | |
| 4,712,547 | A | 12/1987 | Bonnet | |
| 5,292,330 | A | 3/1994 | Shutt | |
| 5,545,175 | A * | 8/1996 | Abidin et al. | 606/182 |
| 6,048,354 | A | 4/2000 | Lawrence | |
| 6,716,228 | B2 * | 4/2004 | Tal | A61B 17/3415 606/167 |
| 7,341,596 | B2 * | 3/2008 | Heppler | 606/167 |
| 2004/0181246 | A1 * | 9/2004 | Heppler | 606/167 |
| 2007/0233151 | A1 * | 10/2007 | Chudik | 606/96 |
| 2009/0157110 | A1 | 6/2009 | Muto et al. | |
| 2011/0087258 | A1 * | 4/2011 | Sluss | 606/170 |

FOREIGN PATENT DOCUMENTS

| CN | 1069644 A | 3/1993 |
| EP | 2311394 A1 | 4/2011 |

OTHER PUBLICATIONS

Matsuda, D.K. "FAI: An emerging problem in orthopedics", Orthopedics Today, Jul. 2009. Retrieved from www.healio.com on Jan. 11, 2013.*
International Search Report and Written Opinion for PCT/US2011/053545 mailed Dec. 19, 2011.
First Office Action for Chinese Patent Application 201180046481.4, issued Feb. 15, 2015.

* cited by examiner

*Primary Examiner* — Kevin T Truong
*Assistant Examiner* — Tracy Kamikawa
(74) *Attorney, Agent, or Firm* — Burns & Levinson LLP; Joseph M. Maraia

(57) ABSTRACT

The present disclosure relates to a method of use during arthroscopic surgery. The method includes inserting a cannulated needle into a joint area of the body, inserting a guidewire through the needle, removing the needle, and inserting an arthroscopy knife into the joint area via the use of the guidewire. An arthroscopy knife and another method of its use is also disclosed.

17 Claims, 5 Drawing Sheets

FIG.1A

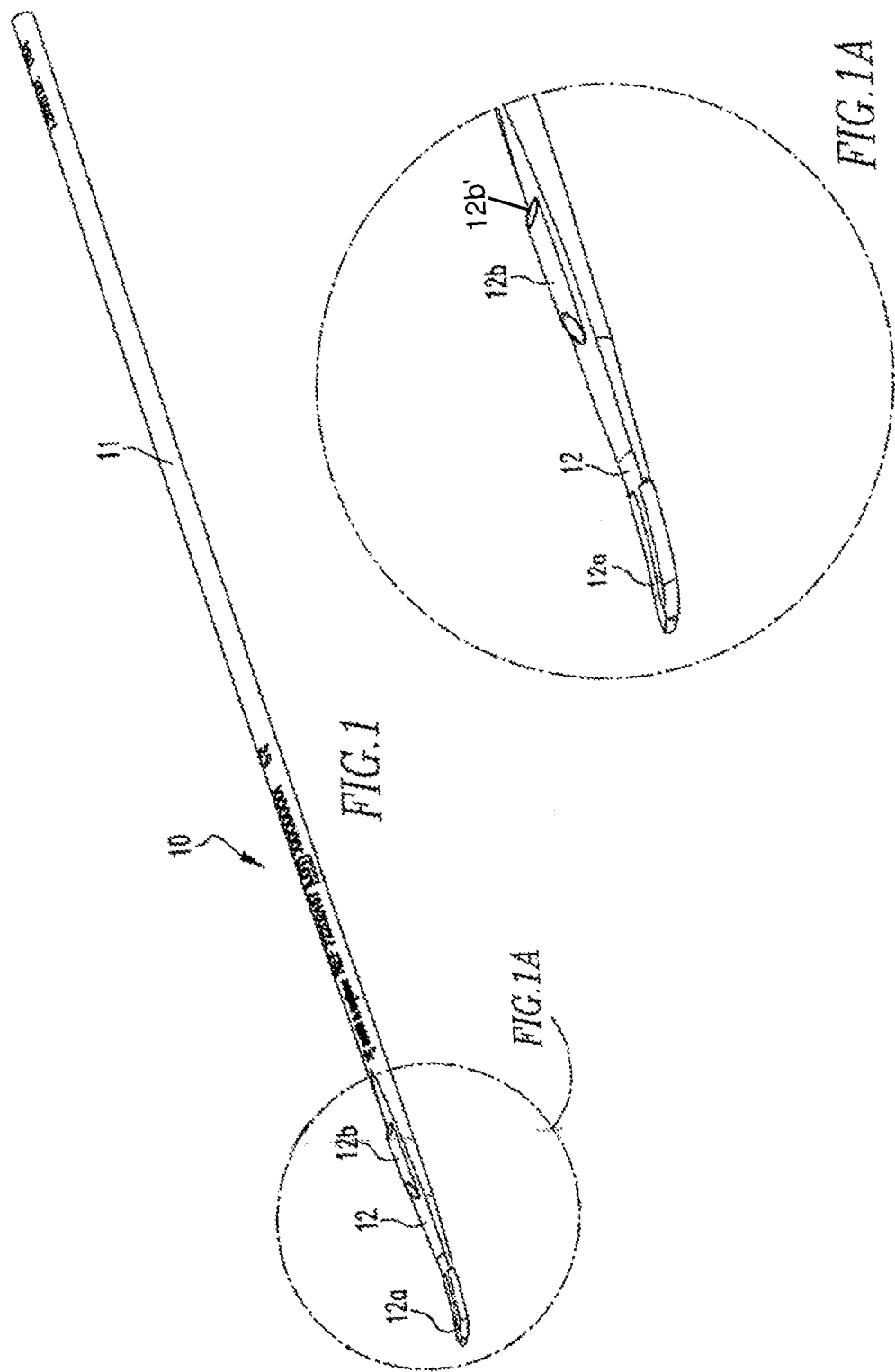

DEVICE AND METHODS FOR USE DURING ARTHROSCOPIC SURGERY

CROSS REFERENCE TO RELATED APPLICATIONS

This application claims priority to U.S. Patent Application Ser. No. 61/386,718, the disclosure of which is incorporated herein by reference in its entirety.

BACKGROUND

1. Field of Technology

The present disclosure relates generally to arthroscopic surgery and, specifically to a device and methods for use during arthroscopic surgery.

2. Related Art

During hip arthroscopy, it is often necessary for a surgeon to use an arthroscopy knife to make incisions that will allow the surgeon to gain access to areas near the hip joint. For example, the knife may be used to detach the labrum from the acetabular rim. During the same procedure, the knife may be used to make an incision in the hip capsule. Using the knife to detach the labrum from the acetabulum has its drawbacks because the point at which the knife will exit the labrum is not known prior to making the cut. Therefore, a knife and specifically, methods of use that allow for more precision control of the knife are needed.

SUMMARY

In one aspect, the present disclosure relates to a method of use during arthroscopic surgery. The method includes inserting a cannulated needle into a joint area of the body, inserting a guidewire through the needle, removing the needle, and inserting an arthroscopy knife into the joint area via the use of the guidewire.

In an embodiment, the method further includes using the knife to detach a portion of the soft tissue from the bone, performing surgery on the bone, and reattaching the detached portion of the soft tissue to the bone. In another embodiment, the knife includes a proximal end and a distal end. In yet another embodiment, the distal end includes a blade and a guidewire component. In a further embodiment, the soft tissue is a labrum and the bone is an acetabulum. In yet a further embodiment, the step of inserting an arthroscopy knife into the joint area via use of the guidewire includes coupling the arthroscopy knife to the guidewire and inserting the knife into the joint area such that a blade of the knife is inserted between the soft tissue and bone. In yet an even further embodiment, coupling the arthroscopy knife to the guidewire includes inserting the guidewire through the component. In an embodiment, the method further comprises using the knife to make an incision in the hip.

In another aspect, the present disclosure relates to an arthroscopy knife. The knife includes a proximal end and a distal end, the distal end including a blade and a guidewire component.

In an embodiment, the distal end is curved. In another embodiment, the guidewire component includes a through hole.

In yet another aspect, the present disclosure relates to a method of use during arthroscopic surgery. The method includes inserting a cannulated needle through a first passage into a joint area of the body; inserting a guidewire through the needle; inserting an arthroscopy knife into the joint area via the use of the guidewire; and creating an incision in a capsule surrounding the joint, the incision located between the first passage and a second passage.

In an embodiment, the method further includes removing the needle after inserting the guidewire. In another embodiment, the method further includes using the knife to detach a portion of soft tissue from bone, performing surgery on the bone, and reattaching the detached portion of the soft tissue to the bone. In yet another embodiment, the knife includes a proximal end and a distal end. In a further embodiment, the distal end includes a blade and a guidewire component. In yet a further embodiment, the soft tissue is a labrum and the bone is an acetabulum. In yet a further embodiment, the step of inserting an arthroscopy knife into the joint area via use of the guidewire includes coupling the arthroscopy knife to the guidewire and inserting the knife into the joint area such that a blade of the knife is inserted between the soft tissue and bone. In an embodiment, coupling the arthroscopy knife to the guidewire includes inserting the guidewire through the component.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings:

FIG. 1 shows a perspective view of the arthroscopy knife of the present disclosure.

FIG. 1A shows an exploded view a distal end of the knife of FIG. 1.

DETAILED DESCRIPTION OF THE EMBODIMENTS

Figure 2A:
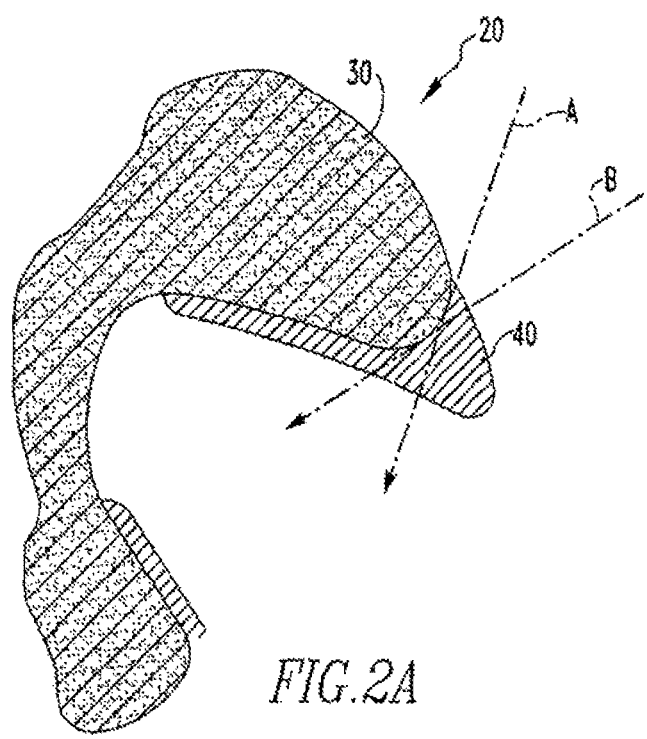
FIGS. 2A-2E show a method of detaching a soft tissue from bone during arthroscopic surgery.

The following description of the preferred embodiment(s) is merely exemplary in nature and is in no way intended to limit the disclosure, its application, or uses.

As shown in FIGS. 1 and 1A, the knife 10 includes a proximal end 11 and a distal end 12. The proximal end 11 is configured for being held by a user, such as a surgeon. The distal end 12 includes a blade 12a and a guidewire component 12b, the purpose of which will be further described below. The distal end 12, especially the blade 12a, may be curved, as shown in FIGS. 1 and 1A. Having a curved distal end 12 biases the blade 12a against a guidewire when the blade 12a is coupled to a guidewire, as is further shown in FIGS. 2A-2E and described below, which minimizes the amount of divergence between the blade 12a and the guidewire. However, a knife 10 having a non-curved distal end may also be used.

Figure 2B:
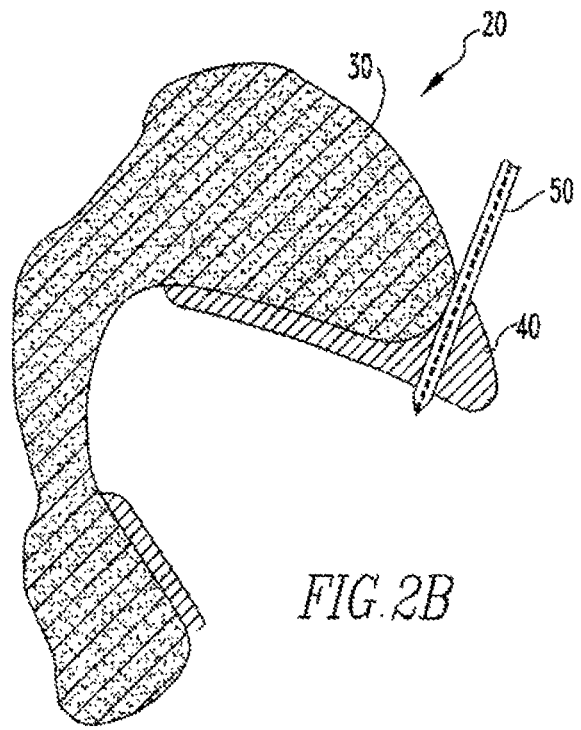
Figure 2C:
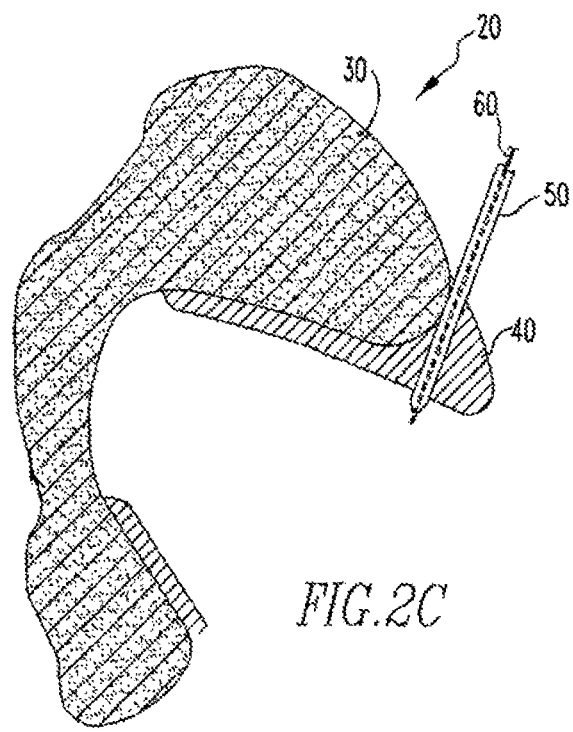
Figure 2D:
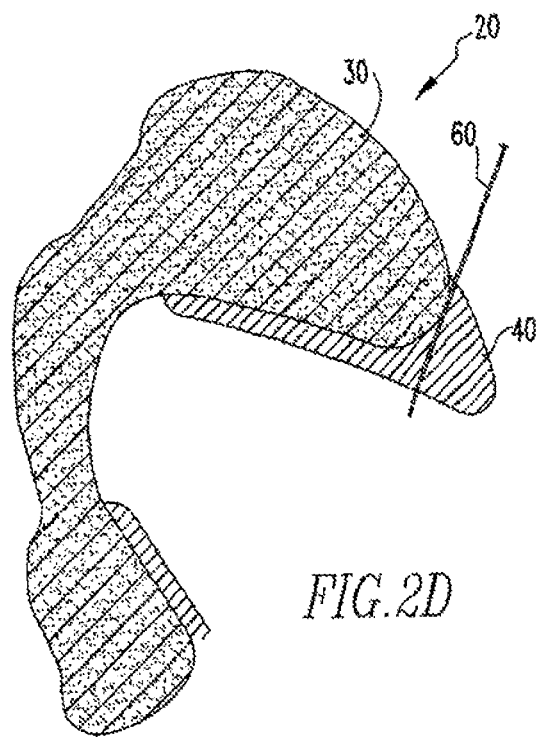
Figure 2E:
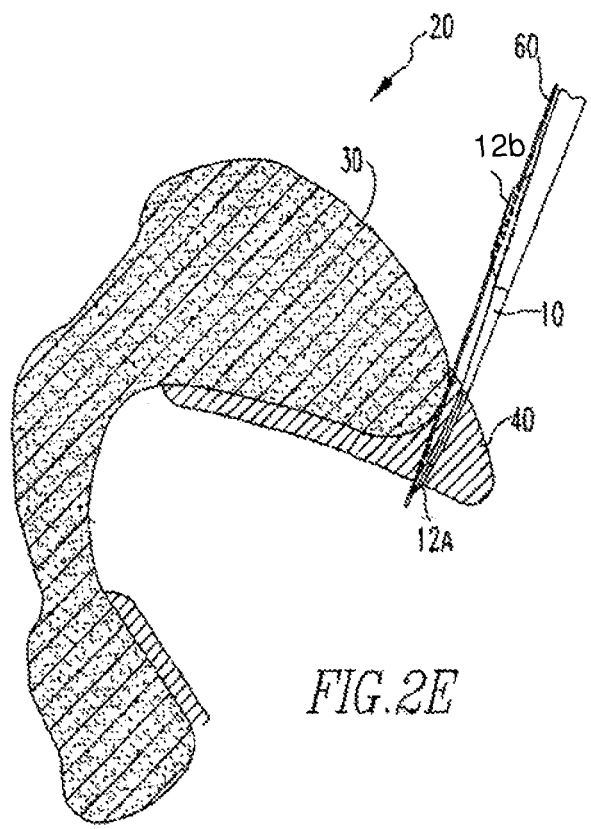

As mentioned above, one of the uses for the knife 10 is detaching soft tissue from bone. Specifically, the knife 10 is used in surgery on the hip joint 20 to detach a labrum 40 from an acetabulum 30, as shown in FIGS. 2A-2E. A cannulated needle 50 is disposed within the joint 20 along one of the trajectories A,B, as shown in FIGS. 2A-2B. Other trajectories may be used. A guidewire 60 is then disposed through the cannulation of the needle 50 and the needle 50 is removed from the joint, as shown in FIGS. 2C and 2D. Subsequently, the knife 10 is inserted into the joint 20 via use of the guidewire 60. Specifically, the knife 10 is coupled to the guidewire 60 by inserting the guidewire 60 through the through hole 12b' of the component 12b and sliding the knife 10 along the guidewire 60 and into the joint 20, such that the blade 12a is located between the acetabulum 30 and the labrum 40, as shown in FIG. 2E. The surgeon operates the knife 10 to cut at least a portion of the labrum 40 away from the acetabulum 30, the purpose of which is to allow access to a portion or portions of the acetabulum 30 where surgery is needed. Subsequently, the knife 10 is removed and surgery on the acetabulum 30 is performed. Once surgery is completed, the detached portion of the labrum 40 is reattached to the acetabulum 30 via the use of soft tissue anchors or other fixation devices known to those of skill in the art.

Figure 3:
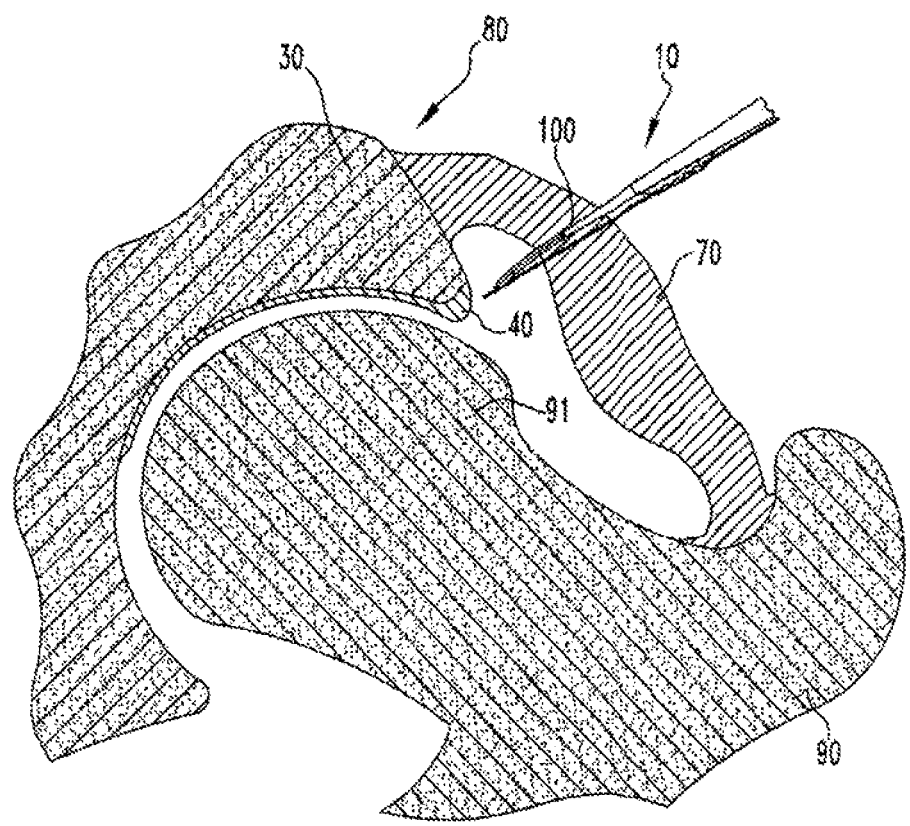
FIG. 3 shows a cross-sectional view of the hip joint while an incision is being made in the hip capsule.

FIG. 3 shows the use of the knife 10 in creating an incision in the hip capsule 70. The capsule 70 is a thick layer of soft tissue surrounding the joint 80, ie the area where the head 91 of the femur 90 is inserted into the acetabulum 30. This thick layer makes changing the trajectory of instruments placed into the joint 80 difficult. For instance, a first instrument (not shown), such as an endoscope, and a second instrument, such as the knife 10, may both be inserted through the capsule 70 and into the joint 80 via the use of separate portals or passages. In order to make the use of these instruments less difficult, an incision or slit may be made in the capsule 70 that would connect the portals and allow for less restricted movement of the instruments. This method of creating an incision in the hip capsule 70 may be used in conjunction with the above-described method of detaching soft tissue from bone. For instance, prior to cutting a portion of the labrum 40 away from the acetabulum 30, the knife 10 may be inserted into the joint area 80, as described above, and then used to create the incision between the knife portal 100 and the endoscope portal.

For purposes of clarity, FIG. 3 only shows a cross-sectional view of the hip joint 80 and the knife passage 100. While the endoscope passage is usually placed within close proximity to the knife passage 100, the endoscope passage may be created anywhere along the capsule 70 that would allow the surgeon to view the surgical area. The passage 100 may also be used for other instruments, such as an anchor delivery device, or other devices used in surgery on the hip joint 80.

For the purposes of this disclosure, the arthroscopy knife 10 is made from a metal material. However, other materials could be used. The knife 10 is made via a process known to one of skill in the art. Additionally, the knife may be used in either manner described above in a joint area other than the hip joint. Furthermore, the incision made in the capsule may be made in other manners. For example, the incision does not have to connect the portals.

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. A method of use during arthroscopic surgery comprising:
    inserting a cannulated needle into a joint area of the body;
    inserting a guidewire through the needle; and
    inserting an arthroscopy knife into the joint area via the use of the guidewire, the knife comprising a distal end including a blade and a guidewire component by which the knife is coupled to the guidewire, and wherein a distal tip of the blade is fixed relative to the guidewire component;
    touching the distal tip of the blade of the knife to the guidewire such that the blade and the guidewire create an angle greater than zero degrees therebetween; and
    wherein the guidewire component receives the guidewire and defines a longitudinal axis of the guidewire which is at an angle relative to and intersects a longitudinal axis of the knife at a point proximal to the distal tip of the blade and distal to a proximal end of the knife, the longitudinal axis of the knife extending from the distal tip of the blade to the proximal end of the knife when the knife is not coupled to the guidewire, such that the blade is biased against the guidewire when the knife is coupled to the guidewire and the distal tip of the blade is touched to the guidewire.

2. The method of claim 1 further comprising removing the needle after inserting the guidewire.

3. The method of claim 1 further comprising:
    using the knife to detach a portion of soft tissue from bone,
    performing surgery on the bone, and
    reattaching the detached portion of the soft tissue to the bone.

4. The method of claim 3 wherein the soft tissue is a labrum and the bone is an acetabulum.

5. The method of claim 1 wherein the step of inserting an arthroscopy knife into the joint area via use of the guidewire includes coupling the arthroscopy knife to the guidewire and inserting the knife into the joint area such that the blade of the knife is inserted between soft tissue and bone.

6. The method of claim 5 wherein coupling the arthroscopy knife to the guidewire includes inserting the guidewire through the component.

7. The method of claim 1, wherein the distal end of the knife is curved.

8. The method of claim 1, wherein the guidewire component includes a through hole.

9. The method of claim 8 wherein the through hole is at an angle relative to a longitudinal axis of the knife.

10. The method of claim 1 further comprising using the knife to make an incision in a hip capsule.

11. The method of claim 1 wherein the biasing is effective to reduce divergence between the blade and the guidewire during the insertion of the knife.

12. A method of use during arthroscopic surgery comprising:
    inserting a cannulated needle through a first passage into a joint area of the body;
    inserting a guidewire through the needle;
    inserting an arthroscopy knife into the joint area via the use of the guidewire, the knife comprising a distal end including a blade and a guidewire component by which the knife is coupled to the guidewire, and wherein a distal tip of the blade is fixed relative to the guidewire component;
    touching the distal tip of the blade of the knife to the guidewire such that the blade and the guidewire create an angle greater than zero degrees therebetween, wherein the guidewire component receives the guidewire and defines a longitudinal axis of the guidewire which is at an angle relative to and intersects a longitudinal axis of the knife at a point proximal to the distal tip of the blade and distal to a proximal end of the knife, the longitudinal axis of the knife extending from the distal tip of the blade to the proximal end of the knife when the knife is not coupled to the guidewire, such that the blade is biased against the guidewire when the knife is coupled to the guidewire and the distal tip of the blade is touched to the guidewire; and creating an incision in a capsule surrounding the joint, the incision located between the first passage and a second passage.

13. The method of claim 12 further comprising removing the needle after inserting the guidewire.

14. The method of claim 12 further comprising:

using the knife to detach a portion of soft tissue from bone, performing surgery on the bone, and reattaching the detached portion of the soft tissue to the bone.

15. The method of claim 14 wherein the soft tissue is a labrum and the bone is an acetabulum.

16. The method of claim 12 wherein the step of inserting an arthroscopy knife into the joint area via use of the guidewire includes coupling the arthroscopy knife to the guidewire and inserting the knife into the joint area such that the blade of the knife is inserted between soft tissue and bone.

17. The method of claim 16 wherein coupling the arthroscopy knife to the guidewire includes inserting the guidewire through the component.

* * * * *